United States Patent [19]

Miwa et al.

[11] 4,347,318

[45] Aug. 31, 1982

[54] METHOD FOR PRODUCING L-THREONINE BY FERMENTATION

[75] Inventors: Kiyoshi Miwa, Matsudo; Takayasu Tsuchida; Osamu Kurahashi, both of Kawasaki; Shigeru Nakamori, Yokohama; Konosuke Sano, Tokyo; Haruo Momose, Kamakura, all of Japan

[73] Assignee: Ajinomoto Company, Incorporated, Tokyo, Japan

[21] Appl. No.: 136,475

[22] Filed: Apr. 2, 1980

[30] Foreign Application Priority Data

Apr. 2, 1979 [JP] Japan .................................. 54-39617

[51] Int. Cl.³ ...................... C12P 13/08; C12N 15/00; C12N 1/20; C12R 1/19
[52] U.S. Cl. .................................... 435/115; 435/172; 435/253; 435/849
[58] Field of Search ........................ 435/115, 172, 253

[56] References Cited

U.S. PATENT DOCUMENTS 3,580,810  5/1971  Shiio et al. ........................ 435/115
4,237,224 12/1980  Cohen et al. ........................ 435/172
4,278,765  7/1981  Debabov et al. .................... 435/172

Primary Examiner—Lionel M. Shapiro
Attorney, Agent, or Firm—Oblon, Fisher, Spivak, McClelland & Maier

[57] ABSTRACT

L-threonine is produced by incorporating into a recipient microorganism of the genus Escherichia which does not require L-threonine for growth, a plasmid, in which a deoxyribonucleic acid fragment which possesses genetic information relating to L-threonine synthesis obtained from a mutant resistant to $\alpha$-amino-$\beta$-hydroxy valeric acid of the genus Escherichia, has been inserted.

4 Claims, No Drawings

METHOD FOR PRODUCING L-THREONINE BY FERMENTATION

This invention relates to a method for producing L-threonine by fermentation.

As to the fermentative production of L-threonine, auxotrophic or drug-resistant mutants of the genera Brevibacterium and Escherichia are known to be used (British Pat. No. 1,223,725, British Pat. No. 1,223,470 and Japanese Published Examined Patent Application No. 44876/1973).

The inventors chose a mutant of the genus Escherichia resistant to α-amino-β-hydroxy-valeric acid (hereinafter referred to as AHV) as the deoxyribonucleic acid (hereinafter referred to as DNA) donor, then obtained from the mutant a DNA fragment possessing genetic information relating to L-threonine synthesis, and finally inserted the DNA fragment into a plasmid obtained from Escherichia coli. The recombinant plasmid was successfully introduced into a microorganism of Escherichia. Further, the inventors have found that the strain having higher L-threonine productivity can be obtained in case a microorganism which does not require L-threonine is used as the recipient of the recombinant plasmid. It was found that the microorganism of this invention produces L-threonine in a yield much higher than hitherto known L-threonine producing mutants.

The mutant of the genus Escherichia resistant to AHV is known (Japanese Published Examined Patent Application No. 26709/1970), and is obtained by usual artificial mutation techniques. Chromosomal DNA is extracted from the mutant by usual manner and treated with restriction endonuclease by usual method. The inventors have used Hind III as the restriction endonuclease to obtain the DNA fragment possessing the genetic information relating to the L-threonine synthesis. However other restriction endonuclease such as Bam HI can be used to obtain analogous results to Hind III.

Any relax-type plasmid extracted from Escherichia coli can be used as the vector DNA. Ordinary manner can be applied for inserting the DNA fragment, which is obtained from AHV-resistant strain of Escherichia and possesses the genetic information related to L-threonine biosynthesis, into the vector. The recombinant plasmid thus obtained can be incorporated into a microorganism of the genus Escherichia by conventional transformation techniques, although the efficiency may differ among these techniques.

As the recipient of the recombinant plasmid, an L-threonine requiring mutant of Escherichia is usually used, since such mutant is convenient for selection and isolation of the transformant. In case a mutant which does not require L-threonine for growth, especially that resistant to AHV, is used as the recipient, L-threonine producing transformants having higher productivity are obtained.

Transformants thus obtained can be selected and isolated by conventional methods based on the characteristics possessed by the vector DNA and/or the recipient.

The methods of culturing the L-threonine producing strain thus obtained are conventional, and are similar to the methods for the cultivation of known L-threonine producing microorganisms. Thus, the culture medium is a conventional one containing carbon sources, nitrogen sources, inorganic ions and, when required, minor organic nutrients such as vitamines or amino acids. Examples of the carbon sources are, glucose, sucrose, starch hydrolysate and molasses. Gaseous ammonia, aqueous ammonia and ammonium salts and others can be used as the nitrogen source. In the case where more than 50 mg/dl of L-aspartic acid is added to the medium, the yield of L-threonine is improved usually.

Cultivation is carried out under aerobic condition adjusting the pH and the temperature of the medium at a suitable level, and continued until the formation of L-threonine ceases.

L-threonine accumulated in the culture medium can be recovered by conventional manners.

According to the present invention, L-threonine can be produced in higher yield than known methods. Moreover, the amount of by-produced amino acids is scarce and, accordingly, L-threonine can be recovered through a simple process in a high yield.

EXAMPLE 1

From L-Threonine producing strain AJ 11332 (FERM-P 4898, NRRL B-12097) (pro−, thi−, ile−, met−, AHVγ) which is derived from Escherichia coli K-12 (ATCC 10798), new strains having high productivity of L-threonine were produced by the following steps:

(1) Preparation of Chromosomal DNA possessing genetic information of high productivity of L-threonine.

Strain AJ 11332 was cultured at 37° C. for 3 hours with shaking in 1 l of L-medium containing 1% peptone, 0.5% yeast extract, 0.1% glucose and 0.5% NaCl, and adjusted to pH 7.2, and bacterial cells in exponential growth phase were collected. Chromosomal DNA was extracted by conventional phenol-method, and 5.3 mg of purified DNA were obtained.

(2) Preparation of vector DNA

For the purpose of cloning of the gene controlling the high productivity of L-threonine (threonine operon containing mutation point of AHV resistance), DNA of plasmid pBR 322, a vector containing both ampicillin and tetracycline resistance genes as makers, was prepared as follows:

A strain of Escherichia coli K-12 harboring the plasmid pBR 322 was incubated at 37° C. in 1 l of a glucose-"casamino acid"-inorganic salts medium added with 170 μg/ml of chloramphemicol. The glucose-"casamino acid"-inorganic salts medium contains, 2 g glucose, 1 g NH$_4$Cl, 6 g Na$_2$HPO$_4$, 3 g KH$_2$PO$_4$, 5 g NaCl, 0.1 g MgSO$_4$.7H$_2$O, 0.015 g CaCl$_2$.2H$_2$O, 20 g "casamino acid", 0.05 g L-tryptophan, 0.05 g thymine and 100 μg thiamine.HCl, perliter, and the pH was adjusted to 7.2. Through this process, the plasmid DNA was amplified and accumulated abundantly in the bacterial cells.

After 16 hours of the incubation, cells were harvested and then lysed by treatment with lysosyme and SDS. The lyzate was centrifuged at 30,000 gX for 1 hour to obtain supernatant. After concentrating the supernatant, 580 μg of the plasmid DNA was obtained by fractionation using cesium chloride-ethidium bromide equilibrium density gradient centrifugation.

(3) Insertion of chromosomal DNA fragment into vector

Each 10 μg of the chromosomal DNA and the vector DNA was treated with restriction endonuclease Hind III at 37° C. for 1 hour to cleave DNA chains, and then heated at 65° C. for 5 minutes, respectively.

The digested chromosomal DNA solution and vector DNA solution were mixed and subjected to the ligation reaction of DNA fragments by the $T_4$ phage DNA ligase in the presence of ATP and dithiothreitol at 10° C. for 24 hours. The reaction mixture was then heated at 65° C. for 5 minutes, and two folds volume of ethanol was added to it. Thus precipitated recombinant DNA was recovered.

(4) Genetic transformation with the hybrid plasmid harboring the genetic information of high threonine productivity An L-threonine-requiring strain of Escherichia coli No. 255 (NRRL B-12265), which was derived from threonine-producing strain AJ 11332 by N-methyl-N'-nitro-N-nitrosoguanidine mutagenesis, was cultured in 10 ml of L-medium at 37° C. with shaking. Cells in exponential growth phase were harvested, and suspended in 0.1 M $MgCl_2$ solution and then in 0.1 M $CaCl_2$ solution in an ice-bath, whereby, "competent" cells having the ability of DNA uptake were prepared. Into the competent cells suspension, the DNA obtained in step (3), which contains the hybrid plasmid DNA, was added. The suspension was kept in an ice-bath for 30 minutes, then heated at 42° C. for 2 minutes, and again allowed to stand in an ice-bath for 30 minutes. The cells, thus being incorporated by the DNA, were inoculated into L-medium and the medium was shaken at 37° C. for 2 hours, whereby the transformation reaction was completed. The cells were collected, washed, and resuspended. A small portion of the cell suspension was spread on an agar plate containing, 2 g glucose, 1 g $(NH_4)_2SO_4$, 7 g $K_2HPO_4$, 2 g $KH_2PO_4$, 0.1 g $MgSO_4 \cdot 7H_2O$, 0.5 g sodium citrate $\cdot 2H_2O$ 20 mg ampicillin, 100 mg L-proline, 100 mg L-isoleucine, 100 mg L-methionine, and 1 mg thiamine $\cdot$ HCl, and 2 g agar, per liter, (pH was adjusted to 7.2). The plate was incubated at 37° C. After 3 days incubation, 21 colonies appeared on the plate. All of the colonies were picked up, purified, and isolated.

Every transformant thus obtained does not require L-threonine and was resistant to ampicillin, which was apparently different in character from strain No. 255 employed as the recipient. This means that only the cells which contained the pBR 322 plasmid being inserted with the chromosomal fragment covering the gene specifying threonine synthesis were selected as growing colonies.

(5) Production of L-threonine by the novel threonine producing strains

Table 1-A shows the experimental result of the fermentative production of L-threonine using strain AJ 11334 (FERM-P 4900, NRRL B-12099) which is one of the clones obtained in step (4).

The fermentation medium contained 3 g/dl glucose, 1 g/dl $(NH_4)_2SO_4$, 0.2 g/dl $KH_2PO_4$, 0.1 g/dl $MgSO_4 \cdot 7H_2O$, 2 ppm $Fe^{++}$, 2 ppm $Mn^{++}$, 1 mg/l thiamine-HCl, 300 mg/l L-proline, 100 mg/l L-isoleucine, 100 mg/l L-methionine, 2 g/dl $CaCO_3$, and the pH was adjusted to 7.0 with KOH. Twenty ml portions of the medium were put into 500 ml flasks, inoculated with AJ 11334, and shaken for 70 hours at 37° C. control experiments were made using the parent strain AJ 11332 under the same culture condition.

As apparent from the Table, AJ 11334 showed remarkably increased productivity of L-threonine, when compared with AJ 11332.

Table 1-B shows an example of the fermentative production of L-threonine using AJ 11333 (FERM-P 4899, NRRL B-12098) which is another clone obtained in step (4). The fermentation medium was prepared by adding 0.1 g/dl of yeast extract to the same medium employed in the experiment of Table 1-A. The cultural condition was the same as that of the experiment of Table 1-A except the temperature of 30° C.

In this case, too, AJ 11333 showed remarkably increased productivity of L-threonine.

TABLE 1

| | Strains | L-threonine produced g/dl |
|---|---|---|
| A | AJ 11334 | 0.54 |
| | AJ 11332 | 0.29 |
| B | AJ 11333 | 0.54 |
| | AJ 11332 | 0.13 |

The amount of threonine was determined by a microbiological essay as to the supernatant obtained by the centrifugation of cultured broth.

(6) Incorporation of the hybrid plasmid into an L-threonine-non-requiring strain.

The hybrid plasmid contained in AJ 11334 was isolated by the method similar to that shown in step (2), and incorporated into the parent strain AJ 11332, which does not require L-threonine for growth, and produces L-threonine, by a transformation technique analogous to that shown in step (4).

The transformant AJ 11335 (FERM-P 4901, NRRL B 12100), selected as an ampicillin resistant colony, was subjected to the fermentative production of L-threonine by the similar method to that described in step (5).

The amount of L-threonine produced and accumulated in the culture medium as well as that of by-product amino acids were determined by liquid chromatography. The results are shown in Table 2.

TABLE 2

| | Amino Acids Accumulated (g/l) | |
|---|---|---|
| Amino Acids | AJ 11332 | AJ 11335 |
| L-threonine | 3.83 | 8.28 |
| L-isoleucine | 0.14 | 0.09 |
| L-homoserine | above 0.2 | not detected |
| L-valine | 0.05 | " |
| L-leucine | 0.02 | " |
| L-proline | below 0.25 | " |
| L-alanine | 0.01 | " |
| L-glutamic acid | above 0.02 | " |
| L-aspartic acid | 0.09 | " |
| L-serine | below 0.2 | " |
| L-lysine | 0.31 | " |
| L-arginine | 0.03 | " |
| L-tyrosine | 0.02 | " |
| L-phenylalanine | 0.06 | " |

EXAMPLE 2

The experiments of the fermentative production were made using AJ 11333 and AJ 11335. The culture media used were that employed in Table 1-A and those prepared by the addition of 0.05 g/dl and 0.1 g/dl of L-aspartic acid to the same medium. The results are shown in Table 3.

TABLE 3

| Strains | L-Aspartic Acid (g/dl) | L-Threonine produced (g/dl) |
| --- | --- | --- |
| AJ 11333 | 0.10 | 0.75 |
| | 0.05 | 0.70 |
| | 0 | 0.46 |
| AJ 11335 | 0.10 | 1.10 |
| | 0.05 | 0.98 |
| | 0 | 0.83 |

What is claimed is:

1. A method for producing L-threonine by fermentation which comprises culturing in a culture medium an L-threonine producing microorganism wherein said microorganism is produced by incorporating into a recipient microorganism of the genus Escherichia which does not require L-threonine for growth, a plasmid, in which a deoxyribonucleic acid fragment which possesses genetic information relating to L-threonine synthesis obtained from a mutant resistant to α-amino-β-hydroxy valeric acid of the genus Escherichia, has been inserted.

2. The method of claim 1 wherein said L-threonine producing microorganism is Escherichia coli NRRL B-12100.

3. The method of claim 1, wherein the culture medium contains L-aspartic acid.

4. A bacterium of the genus Escherichia which is Escherichia coli NRRL B-12100.

* * * * *